(12) United States Patent
Persson

(10) Patent No.: US 7,370,654 B2
(45) Date of Patent: May 13, 2008

(54) TRACHEOSTOMA VALVE

(75) Inventor: Jan-Ove Persson, Höör (SE)

(73) Assignee: Atos Medical AB, Horby (SE)

( * ) Notice: Subject to any disclaimer, the term of this patent is extended or adjusted under 35 U.S.C. 154(b) by 733 days.

(21) Appl. No.: 10/292,598

(22) Filed: Nov. 13, 2002

(65) Prior Publication Data

US 2004/0089291 A1    May 13, 2004

(51) Int. Cl.
*A61M 16/00*    (2006.01)

(52) U.S. Cl. .............................. 128/207.16; 128/207.14

(58) Field of Classification Search ........... 128/207.12, 128/207.14, 207.16, 911, 912, 201.13
See application file for complete search history.

(56) References Cited

U.S. PATENT DOCUMENTS

| | | | | |
|---|---|---|---|---|
| 4,325,366 A | * | 4/1982 | Tabor ..................... | 128/207.16 |
| 4,809,693 A | * | 3/1989 | Rangoni et al. ....... | 128/207.16 |
| 5,059,208 A | * | 10/1991 | Coe et al. ...................... | 623/9 |
| 5,107,828 A | * | 4/1992 | Koss et al. ............. | 128/200.26 |
| 5,647,355 A | * | 7/1997 | Starr et al. ............. | 128/205.24 |
| 5,738,095 A | * | 4/1998 | Persson ................... | 128/207.14 |
| 5,765,560 A | * | 6/1998 | Verkerke et al. ....... | 128/207.16 |

FOREIGN PATENT DOCUMENTS

EP    0187461    7/1986

\* cited by examiner

*Primary Examiner*—Michael J. Hayes
*Assistant Examiner*—Michael G. Mendoza

(57) ABSTRACT

A tracheostoma valve adapted to control the flow of air through a tracheostoma comprising a tubular housing having an open first end to be connected to the tracheostoma, and forming at least one side opening in the wall thereof, a shut-off valve member, and a normally closed cough valve member is disclosed. The shut-off valve member comprises a flexible diaphragm mounted in the housing and shaped to normally assume a curled position spaced from the inside surface of the housing wall to allow air flow through the housing and the side opening from trachea to the ambient atmosphere, and to engage said the surface, closing the side opening, at a predetermined air flow rate. The cough valve member controls an open second of the housing to open in response to a particular pressure achieved in the housing and to close automatically at reduction of the air pressure.

15 Claims, 3 Drawing Sheets

TRACHEOSTOMA VALVE

This application claims the benefit of International Application No. PCT/SE01/01090 filed May 17, 2001.

BACKGROUND OF THE INVENTION

1. Field of the Invention

The invention relates to a tracheostoma valve adapted to control the flow of air through a tracheostoma comprising a tubular housing having a first end and a second end, said first end being open to be connected to the tracheostoma, a shut-off valve member normally open to allow air flow through the housing from said first end to the ambient atmosphere and closing at a predetermined air flow rate, and a normally closed cough valve member controlling an opening at said second end to open in response to a particular pressure achieved in said housing and to close automatically at reduction of the air pressure.

Due to deceases of different kinds it is sometimes necessary to remove the larynx by surgery and to open a tracheostoma in order that the individual exposed to the surgery can breath. By the removal of the larynx the ability to speak will be lost but can be restored to some extent by means of another surgery wherein a fistula is opened up between trachea and esophagus to pass air to the oral cavity via the fistula. A one-way valve is mounted in the fistula. This valve referred to as a voice prosthesis, allows air to pass from trachea to esophagus but blocks completely flow in the opposite direction. For speech to be generated the tracheostoma must be closed so that air can be pressed from trachea via the voice prosthesis into esophagus the mucous membranes of which are made to vibrate so that speech is produced. The tracheostoma can be closed by covering the tracheostoma with a finger but it is more convenient to use for this purpose a tracheostoma valve of the kind referred to above, which is attached to the neck of the person that has been exposed to tracheostoma surgery, in order to control the connection between trachea and the ambient atmosphere via the tracheostoma. The tracheostoma valve provides a hands-free control of said connection and the following further advantages:

the tracheostoma will not be obstructed by clothing and, therefore, the tracheostoma valve can be carried more discreetly under a shirt or the like;

the body will promote warming and moistening of the inhalation air;

clothes located in front of the tracheostoma valve will not be soaked by humidity and phlegm.

2. Description of the Prior Art

A tracheostoma valve of the kind referred to above is disclosed in EP-B1-0 617 630. In this prior art embodiment the shut-off valve member and the cough valve member are both constructed as pivoted flaps. The flap forming the cough valve member keeps the opening at said second end of the housing normally closed and forms an opening which is normally open but will be closed by the flap forming the shut-off valve member at said predetermined air flow. The flaps are held in the closed and open position, respectively, by permanent magnets. The shut-off valve flap suffers from the drawback that it will not close until the magnet force is lower than the force produced by the air flow at powerful expiration causing big noise when the flap closes against an associated seat. A further disadvantage of this prior art tracheostoma valve is that the proper function thereof is dependent of the position of the person using the valve; the valve functions in a proper way only when the person holds the head in a substantially vertical position because the function of the valve is based partially on gravity.

U.S. Pat. No. 4,582,058 describes a tracheostoma valve wherein the function of the shut-off valve member is controlled by spring bias. According to U.S. Pat. No. 5,059,208 the shut-off valve member comprises a flexible curled membrane of rubber. These prior art tracheostoma valves require a relatively high pressure in the housing for keeping the shut-off valve in the closed position during speech, which means that it may be difficult to terminate a sentence when the expiration air from the lungs is ebbing due to the fact that the shut-off valve is unintentionally opening to early.

BRIEF SUMMARY OF THE INVENTION

The problems encountered in using the prior art tracheostoma valves discussed above are overcome by the tracheostoma valve of the invention which according to claim 1 is characterized in that the wall of said housing forms at least one side opening, and that said shut-off valve member comprises a flexible diaphragm mounted in said housing and shaped to normally assume a curled position spaced from the inside surface of said wall, and to engage said surface, closing said at least one side opening, at said predetermined air flow rate.

Further advantageous features of the tracheostoma valve of the invention are defined in the dependent claims.

BRIEF DESCRIPTION OF THE DRAWING

An illustrative embodiment of the tracheostoma valve of the invention will be described below reference being made to the accompanying drawing in which.

DETAILED DESCRIPTION OF THE INVENTION

Figure 1:
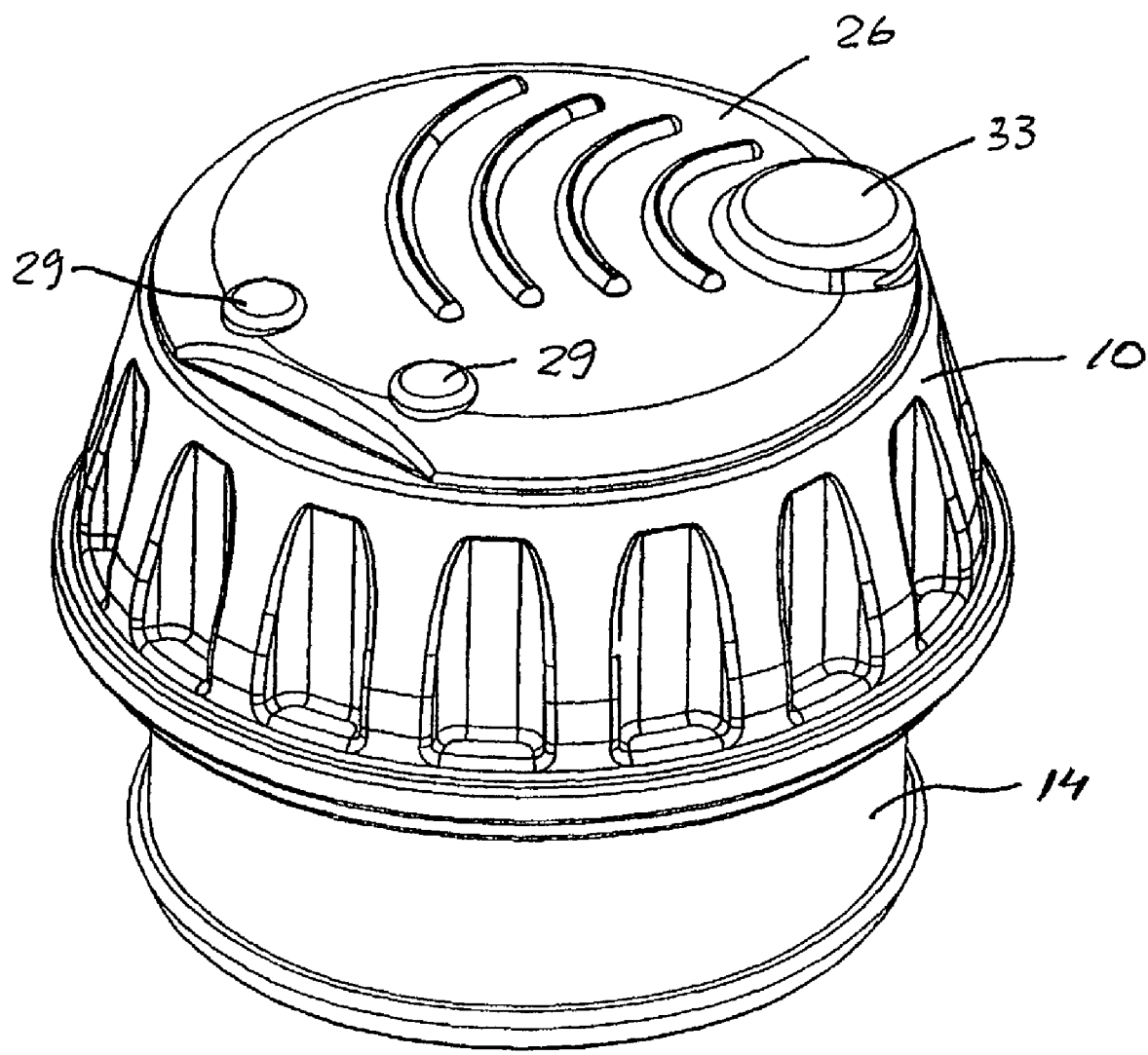
FIG. 1 is a perspective view of the tracheostoma valve.
Figure 2:
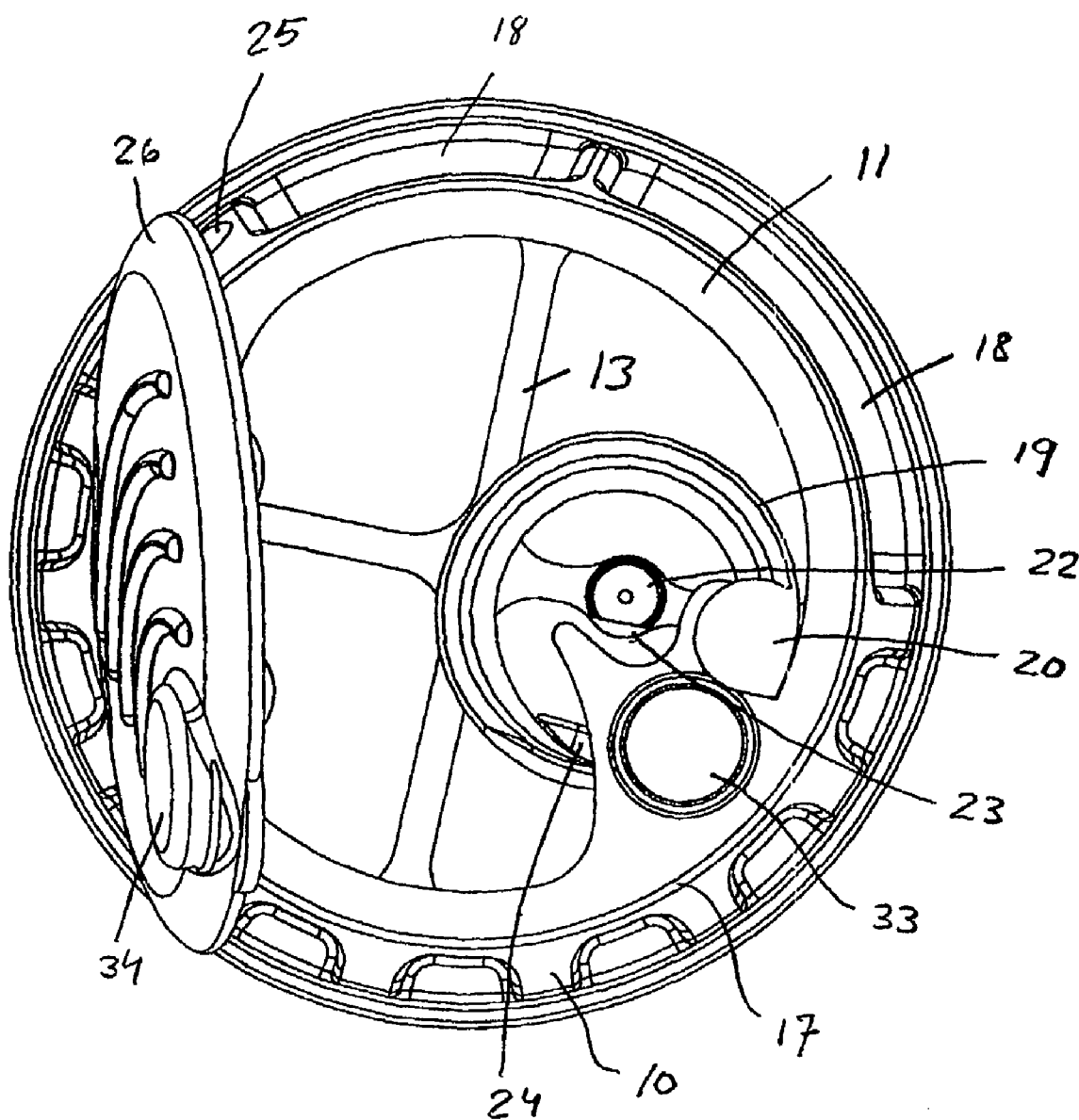
FIG. 2 is a plan view of the valve with the cough valve member in open position.
Figure 3:
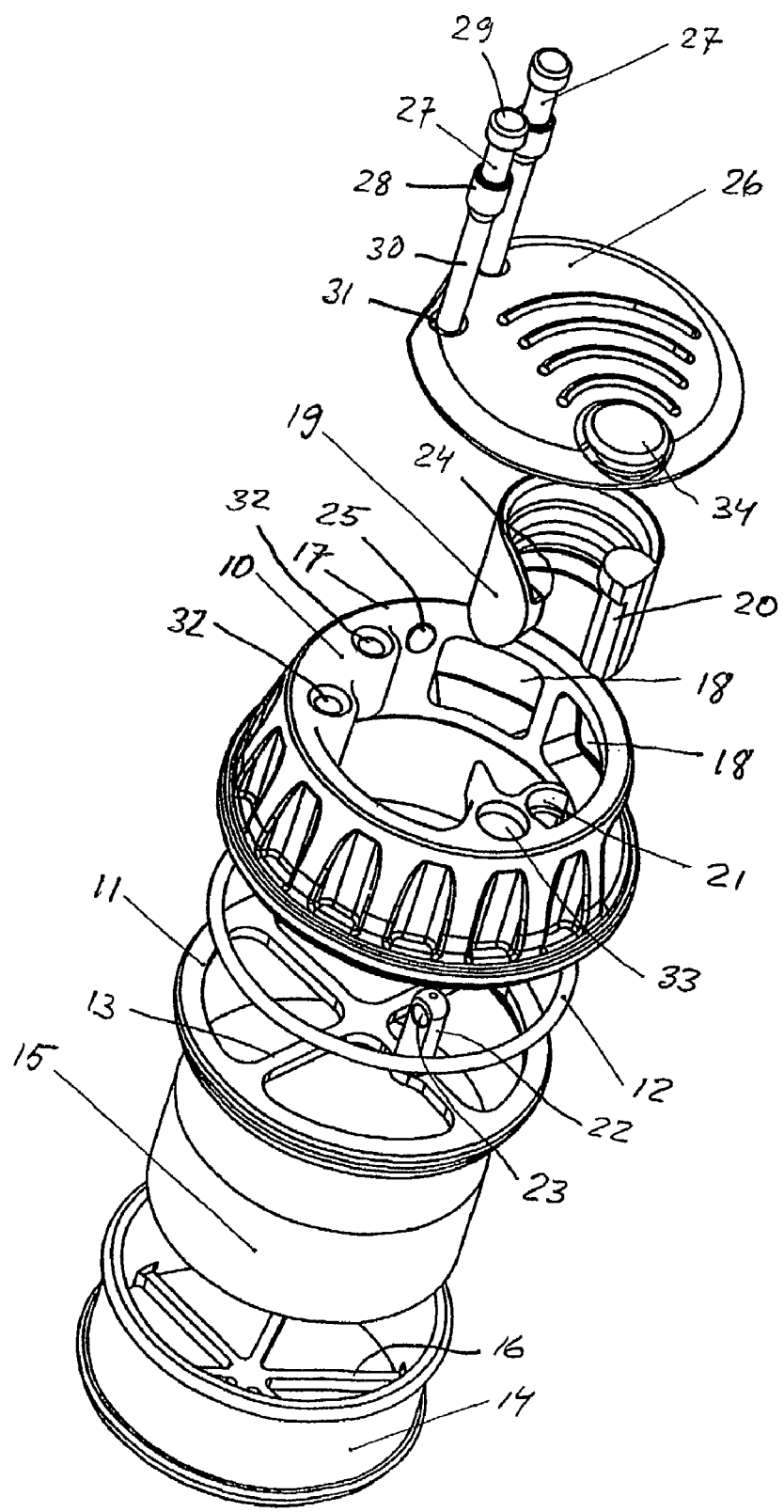
FIG. 3 is an exploded view of the valve.

The handsfree tracheostoma valve disclosed in the drawing comprises a circular housing 10 which can be made of plastics material and is open at each end thereof. At one open end the housing is rotatably connected to a metal holder 11 by an inwardly protruding edge of the housing being received in an outside circumferential groove in the holder, a sealing ring 12 being located between the housing and the holder. The holder forms a spider 13 allowing air to pass therethrough. The valve is combined with a heat and moisture exchange unit (HME unit) including a cassette 14 and a plastic foam body 15 with open cells and impregnated with calcium chloride. The cassette is demountably connected with the holder 11 at a proximal open end of the cassette by snap locking into an inside groove in the holder 11. The foam body is enclosed by the cassette 13 between a spider 16 at the other end thereof and the holder. The Latter end of the cassette is intended to be connected to an adapter on a self-adhesive plaster to be attached to the person's neck over the tracheostoma, or to a laryngectomy tube to be inserted into trachea through the tracheostoma. The HME unit should be made for one way use preferably of a plastics material which is deformed at demounting of the HME unit from the holder so that the unit after demounting cannot be used again. It is advantageous that the HME unit is connected to the distal end of the housing and not—as is usual in prior art tracheostoma valves—to the proximal end of the housing because the unit then prevents cough secretion to enter the tracheostoma valve, which may disturb the function of the valve and may necessitate troublesome cleaning thereof. If it should happen that a part of the tracheostoma valve after long time use of the valve loosens therefrom, the HME unit prevents such part from falling into the lungs.

The housing 10 forms a side wall 17 with side openings 18. A flexible membrane 19 of rubber or similar elastic material is normally curled as shown in FIG. 1. It has at one edge thereof a bead 20 and is mounted in the housing 10 by the bead being slid into an undercut axial slot 21 inside the housing so that the membrane can be easily exchanged if desired. The membrane 19 is a shut-off valve member, which in the curled condition shown leaves the openings 18 open so that there is a free communication between the interior of the housing and the ambient atmosphere through the side openings. On the spider 13 an upstanding pin 22 integral with the holder 11 is provided with a permanent magnet 23 at the upper end thereof, and another permanent magnet 24 is provided at the free end of the membrane 19 for cooperation with the magnet 23. By adjustment of the rotary position of the housing 10 in relation to the holder 11 the magnets can be brought close to each other so that the magnets are attracted to each other by the magnet force to releasably hold the membrane 19 in the curled condition shown, or the magnets may be mutually spaced so that the membrane is held in the curled condition by its own. The membrane can be rolled out from the curled condition so as to engage the inside surface of the side wall 17 and cover the side openings 18, and a permanent magnet 25 is mounted in the housing to hold in cooperation with the magnet 24 the membrane in this closed position.

A cover 26 is hingedly connected to the housing 10 to cover the other proximal open end thereof by means of elastic strings 27 of silicone rubber each of which has enlarged portions 28 and 29. A tail 30 formed by the string is passed through an aperture 31 in the cover and an aperture 32 in the housing said openings having a smaller diameter than the enlarged portions 28 and 29. The string is then pulled at the tail 30 so that the enlarged portion 28 is urged through apertures 31 and 32, the enlarged portion 29 being located on the upper side of the cover at aperture 31. The strings form a hinge between the cover 26 and the housing 10, and the distance between the enlarged portions 28 and 29 is such that the strings are under tension between said portions and as a consequence thereof bias the cover to the closed position. The tail 30 is cut off after mounting of the cover. A permanent magnet 32 is mounted in the housing and cooperates with a permanent magnet 34 on the cover to keep the cover in a closed position.

In the normal condition of the tracheostoma valve described the cover 26 forming the cough valve member of the valve is in the closed position shown in FIG. 1 and is held in this position by the magnets 33 and 34 when the person using the tracheostoma valve is breathing normally. Under these circumstances the membrane 19 is in the curled condition so that the openings 18 are unobstructed, and the housing 10 is in a rotated position in which the magnets 23 and 24 are not attracted to each other. During breathing inhalation air passes from the ambient atmosphere through the openings 18 into the housing and from there via the spider 13 through the HME unit 14, 15 into trachea and then to the lungs. During expiration the breathing air follows the same path in the opposite direction. As long as the breathing is normal, i.e. the air flow rate is below a predetermined value, the membrane will not be brought to the closing position during expiration. However, if the person wishes to produce speech by pressing expiration air through a voice prosthesis he increases the expiration air flow rate over the said predetermined value so that the membrane 19 is rolled out and closes the openings 18. The membrane provides silent successive closing of the side openings. When the side openings are closed no expiration air can pass through the tracheostoma valve to the ambient atmosphere; the air will instead be passed through the voice prosthesis to the oral cavity and from there through the mouth to the ambient atmosphere under creation of speech. The membrane will be releasably kept in the closed position by the magnets 24 and 25 so that the person will be able to completely utilize the expiration phase for speech; there is accordingly no risk of the membrane returning to the open position before a sentence has been completed. When the person initiates a new inhalation phase in order to breath normally again the membrane is pulled from closed to open position the magnet force between the magnets 24 and 25 being overcome.

When the person using the tracheostoma valve breathes more heavily due to physical effort such as exercise, walking on stairs etc. the membrane could move to the closing position during expiration and thus could obstruct the expiration. In order to avoid this the person adjusts the housing 10 to a rotated position wherein the magnets 23 and 24 are close to each other and accordingly are mutually attracted in order to hold the membrane 19 releasably in the open position against the force acting on the membrane in closing direction by the expiration air at heavy breathing.

The cover 26 forming the cough valve member of the tracheostoma valve normally is held in the closed position by the magnets 34 and 33. If the pressure in the housing 10 increases over a particular value as at coughing which would bring the membrane 19 to closing position the communication between the interior of the tracheostoma valve and the ambient atmosphere thus being interrupted, the attraction force between the magnets 33 and 34 will be overcome so that the cover will be moved to the open position and air can escape from the housing to the ambient atmosphere. At pressure reduction in the housing 10 the cover 26 will return to the closed position under the spring bias provided by the strings 27 forming the hinge of the cover, and will again be held in the closed position by the magnets 33 and 34. The particular pressure in the housing at which the cover 26 opens should be adjustable and such adjustment can be effected by adjustment of the spacing between the magnets 33 and 34 with the cover in the closed position. For this purpose screw means can be provided for the magnet 33 for adjustment of the axial position thereof. The cover 26 should have a low weight so that it opens and closes very rapidly at an attack of coughing, which minimizes the trauma felt by the person carrying the tracheostoma valve.

The air flow rate at which the membrane 19 closes at normal breathing must be individually adapted to the person using the tracheostoma valve. The mounting of the membrane makes it easily exchangeable so that it is easy to try out a membrane with the closing properties which are best suited for the person in question; a soft membrane closes more easily than a hard membrane. Also, the force produced by the permanent magnets should be chosen with due consideration of the desired functional characteristics of the membrane 19 and the cover 26, respectively, in order to have the tracheostoma valve functioning as described above.

Instead of having two cooperating magnets it is possible to provide in each case a single permanent magnet which cooperates with a mumber of a metal that can be attracted magnetically by the magnet. A device of this kind is equivalent with two cooperating magnets in connection with the invention.

The invention claimed is:

1. A tracheostoma valve adapted to control the flow of air through a tracheostoma comprising:
    a tubular housing having a first end and a second end, said first end being open and to be connected to the tracheostoma;
    a shut-off valve member normally open to allow air flow through the housing from said first end to the ambient atmosphere and closing at a predetermined air flow rate;
    a normally closed cough valve member controlling an opening at said second end to open in response to a particular pressure achieved in said housing, and to close automatically at reduction of the air pressure,
    wherein a wall of said housing forms at least one side opening, and the shut-off valve comprises a flexible diaphragm mounted in said housing and shaped to normally assume a curled position spaced from the inside surface of said wall, and to engage said surface, closing said at least one side opening, at said predetermined air flow rate.

2. The tracheostoma valve according to claim 1, further comprising:
    a permanent magnet device for releasably maintaining the diaphragm in the closed position.

3. The tracheostoma valve according to claim 2, wherein the permanent magnet device comprises a first permanent magnet on the diaphragm and a cooperating second permanent magnet on the inside surface of the wall of the housing.

4. The tracheostoma valve according to claim 1, further comprising:
    a permanent magnet device for releasably maintaining the diaphragm in the open position.

5. The tracheostoma valve according to claim 1, wherein the housing is rotatably mounted on a holder.

6. The tracheostoma valve according to claim 4, wherein the permanent magnet device comprises a first permanent magnet on the diaphragm and a cooperating second permanent magnet on the holder.

7. The tracheostoma valve according to claim 6, wherein the spacing between the first and second magnets is adjustable by rotating the housing of the holder.

8. The tracheostoma valve according to claim 1, wherein the cough valve member comprises a cover closing the opening of the housing at said second end thereof.

9. The tracheostoma valve according to claim 8, wherein an elastic hinge is provided between the cover and the housing biasing the cover to the closed position.

10. The tracheostoma valve according to claim 9, wherein a permanent magnet device releasably maintains the cover in the closed position.

11. The tracheostoma valve according to claim 10, wherein the permanent magnet device comprises a first permanent magnet on the diaphragm and a cooperating second permanent magnet on the cover.

12. The tracheostoma valve according to claim 11, wherein the first permanent magnet on the housing is mounted for adjustment of the spacing between the first and second permanent magnets.

13. The tracheostoma valve according to claim 1, further comprising:
    a heat and moisture exchanging unit mounted over the opening at said first end of the housing.

14. The tracheostoma valve according to claim 13, wherein said heat and moisture exchanging unit provides means for mounting the tracheostoma valve to an adapter on a plaster to be attached to the user's neck over the tracheostoma.

15. The tracheostoma valve according to claim 13, wherein said heat and moisture exchanging unit provides means for mounting the tracheostoma valve to a larynge tube to be inserted through the tracheostoma.

* * * * *